(12) United States Patent
Kobayashi

(10) Patent No.: US 9,025,055 B2
(45) Date of Patent: May 5, 2015

(54) IMAGE PROCESSING APPARATUS, IMAGE PROCESSING METHOD AND RADIATION SYSTEM

(71) Applicant: Canon Kabushiki Kaisha, Tokyo (JP)

(72) Inventor: Tsuyoshi Kobayashi, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 67 days.

(21) Appl. No.: 13/785,159

(22) Filed: Mar. 5, 2013

(65) Prior Publication Data

US 2013/0235236 A1 Sep. 12, 2013

(30) Foreign Application Priority Data

Mar. 12, 2012 (JP) ................................ 2012-055093

(51) Int. Cl.
H04N 9/64 (2006.01)
H04N 5/20 (2006.01)
H04N 5/361 (2011.01)
H04N 5/217 (2011.01)
A61B 6/00 (2006.01)
G06T 5/50 (2006.01)
G06T 5/00 (2006.01)

(52) U.S. Cl.
CPC ............. *H04N 5/361* (2013.01); *H04N 5/2176* (2013.01); *A61B 6/4233* (2013.01); *A61B 6/585* (2013.01); *G06T 5/50* (2013.01); *G06T 5/002* (2013.01)

(58) Field of Classification Search
CPC ....................................................... H04N 5/361
USPC ................. 348/243, 245, 246, 247, 248, 249, 348/250–252, 255
See application file for complete search history.

(56) References Cited

U.S. PATENT DOCUMENTS

| 6,751,289 | B2 * | 6/2004 | Aoki et al. | 378/98.7 |
| 7,196,725 | B1 | 3/2007 | Saigusa et al. | 348/245 |
| 7,812,865 | B2 * | 10/2010 | Tsuruoka | 348/241 |
| 8,090,181 | B2 | 1/2012 | Omi | 382/132 |
| 8,249,325 | B2 * | 8/2012 | Omi | 382/132 |
| 2005/0099515 | A1 * | 5/2005 | Tsuruoka | 348/241 |
| 2009/0202129 | A1 * | 8/2009 | Omi | 382/132 |

FOREIGN PATENT DOCUMENTS

| EP | 1533997 | 5/2005 |
| EP | 2148500 | 1/2010 |

(Continued)

OTHER PUBLICATIONS

T. Bruijns et al., "Technical and Clinical Assessments of an Experimental Flat Dynamic X-ray Image Detector System", *SPIE Conference on Physics of Medical Imaging*, vol. 3659, pp. 324-335 (Feb. 1999).
EESR issued on in counterpart EPA 13157486.

*Primary Examiner* — Ahmed A Berhan
(74) *Attorney, Agent, or Firm* — Fitzpatrick, Cella, Harper & Scinto

(57) ABSTRACT

An image processing apparatus for a radiation image obtains radiation image data obtained using a radiation detector, and dark current data based on a signal obtained from the radiation detector while no radiation is being emitted from the radiation generator. The image processing apparatus generates correction data by changing a ratio of frequency components based on the dark current data, and corrects the radiation image data based on the generated correction data.

21 Claims, 7 Drawing Sheets

(56) References Cited

FOREIGN PATENT DOCUMENTS

| JP | 10-098651 | 4/1998 |
| JP | 11-331592 | 11/1999 |
| JP | 2003-244557 | 8/2003 |
| JP | 2008-236661 | 10/2008 |
| JP | 2009-189440 | 8/2009 |
| JP | 2009-279042 | 12/2009 |

* cited by examiner

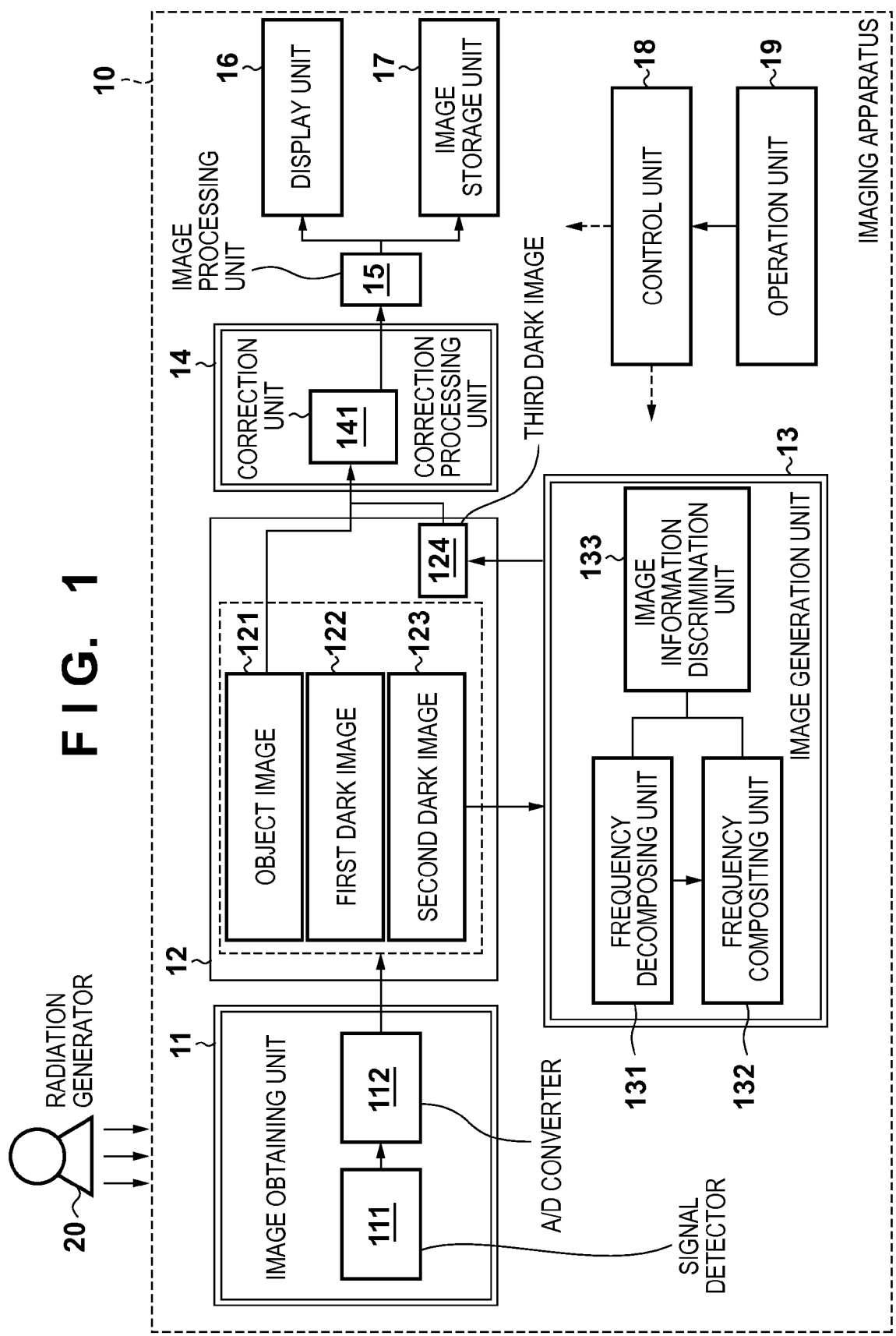

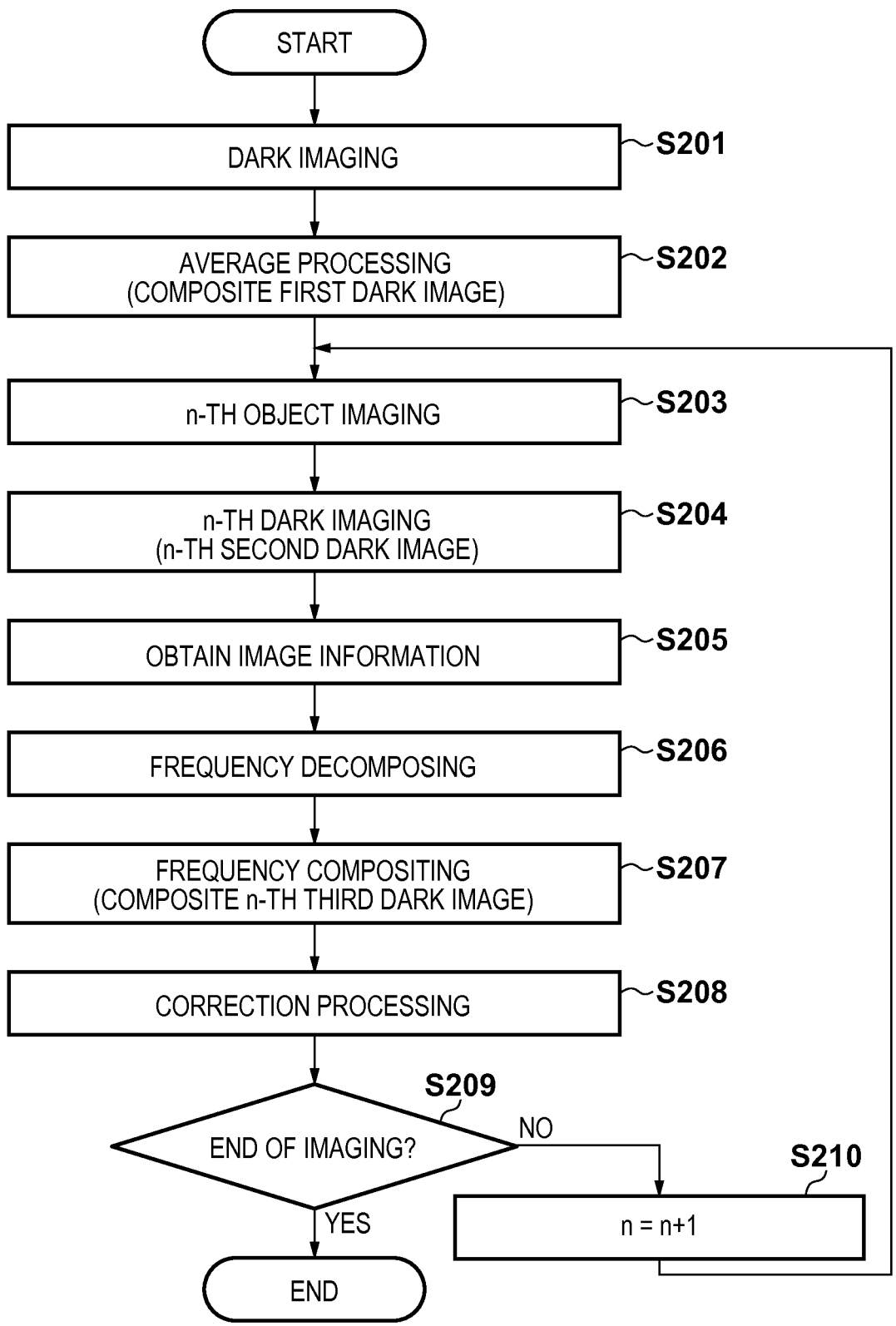

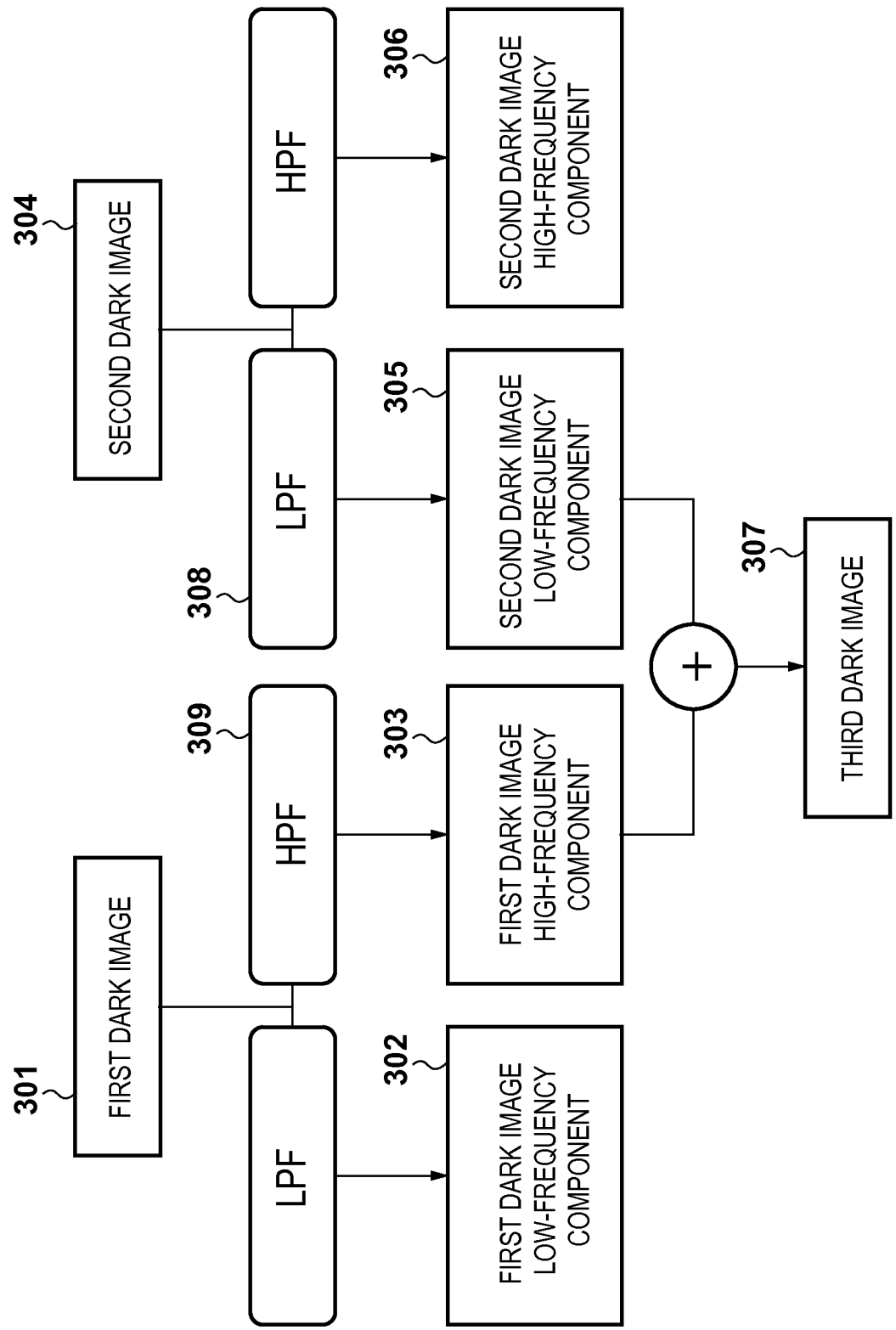

F I G. 5C
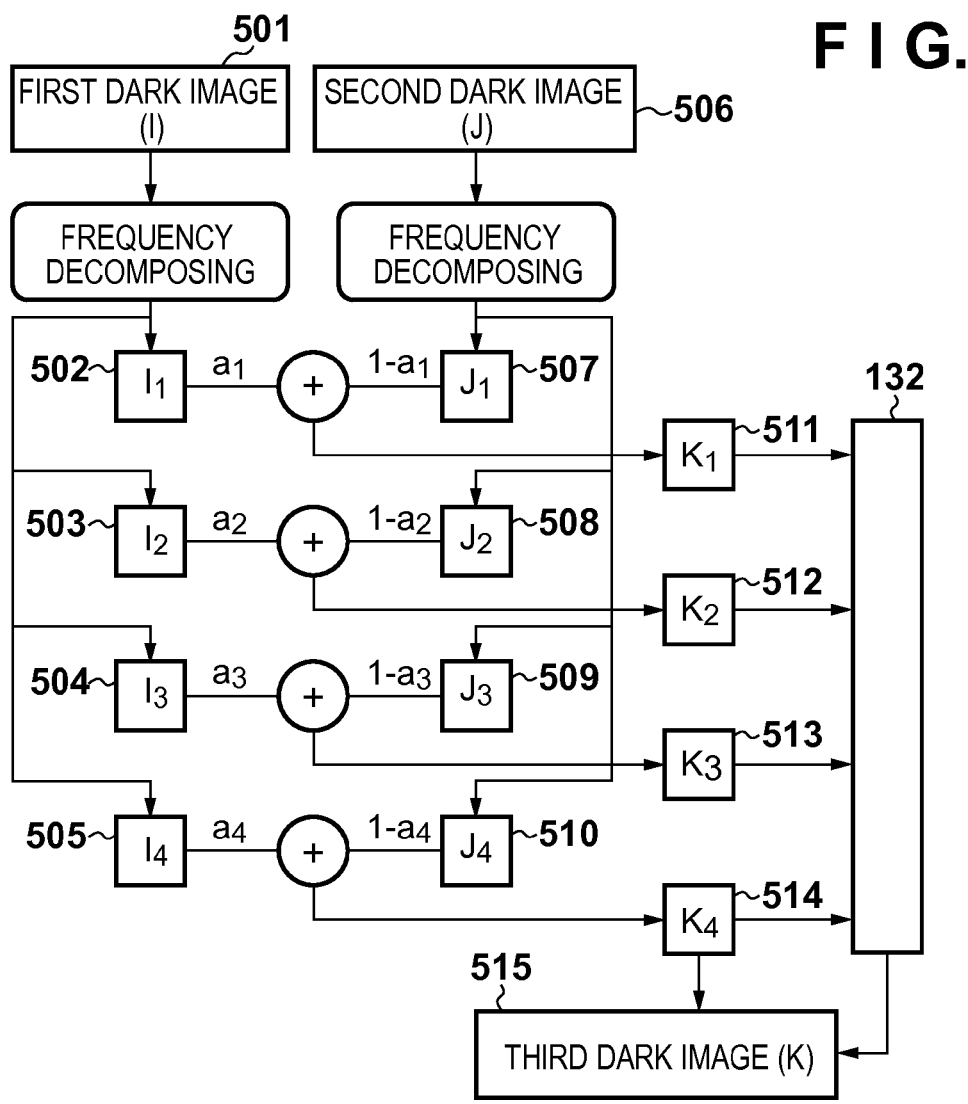
F I G. 5D
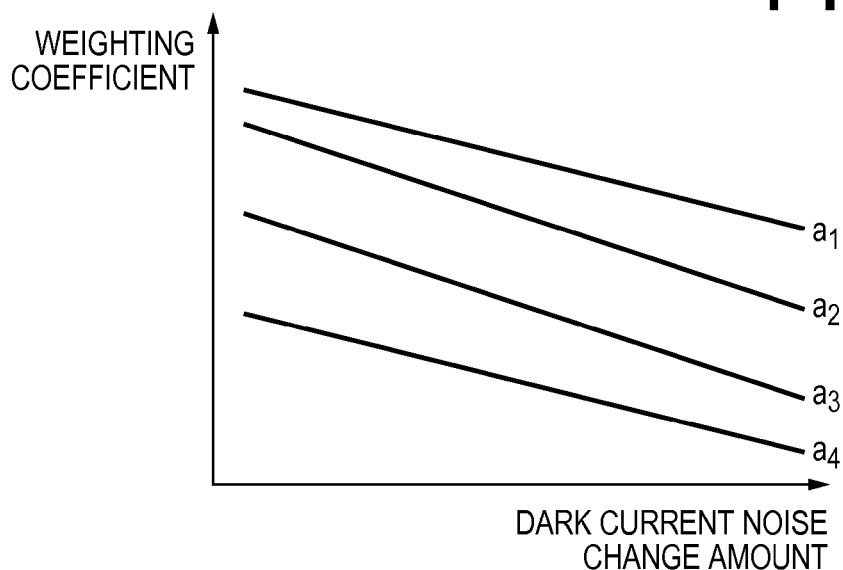

IMAGE PROCESSING APPARATUS, IMAGE PROCESSING METHOD AND RADIATION SYSTEM

BACKGROUND OF THE INVENTION

1. Field of the Invention

The present invention relates to an image processing apparatus, an image processing method and a radiation system, and more specifically to a removal technique of dark current noise in a captured image.

2. Description of the Related Art

An imaging apparatus using a large-scale sensor, which is configured by two-dimensionally arranging solid-state imaging elements each made up of single-crystal silicon or amorphous silicon, has been prevalently put into practical use. Such imaging apparatus is used not only to capture a visible light image in, for example, a digital camera but also to capture a radiation image in a medical apparatus.

As is known, in the imaging apparatus, dark current noise is generated due to variations of dark currents of elements even in a non-exposure state. For this reason, when output signals of imaging elements are used intact, dark current noise is unwantedly superposed on effective signal components, thus causing deterioration of image quality.

In order to remove such dark current noise, a method of obtaining a dark image by performing imaging in a non-exposure state (to be referred to as "dark imaging" hereinafter), and subtracting the dark image from an exposure image is known. The invention described in Japanese Patent Laid-Open No. 2003-244557 (to be referred to as "literature 1" hereinafter) has proposed a method of removing dark current noise by performing dark imaging under the same condition every time an image of an object is captured. Also, the invention described in Japanese Patent Laid-Open No. 2008-236661 (to be referred to as "literature 2" hereinafter) has proposed a method of removing dark current noise without performing dark imaging for each imaging by obtaining dark image data in advance. Furthermore, Japanese Patent Laid-Open No. 2009-279042 (to be referred to as "literature 3" hereinafter) has a method of compositing dark image data, which is held in advance before imaging and that obtained for each imaging at a predetermined ratio.

Dark current correction by changing a ratio of image components having specific image information in association with dark image data and other image components is often not successful. For example, in the technique of literature 1, an exposure image and a dark image are both required to be used. However, since each image has further random noise components, these noise components are superposed when the subtraction is performed. As a result, random noise components are increased by a factor of √2 times, thus in fact lowering the signal-to-noise ratio after correction. This influences image quality in a region in which the signal is small and is relatively close to the noise level. Especially, in a radiation imaging apparatus which requires low-dose imaging, such increased random noise influences diagnosis performance.

For example, in the technique of literature 2, dark current noise components can only be extracted before imaging. For this reason, when dark current noise components vary due to a change in operation temperature of the imaging apparatus during imaging or generation of an afterimage caused by exposure, correction cannot be performed with sufficiently high precision. Thus, components which cannot be corrected appear as an artifact on an image.

Furthermore, the technique of literature 3 does not specify that coefficients are set for respective image components of dark image data.

SUMMARY OF THE INVENTION

According to one aspect of the present invention there is provided an image processing apparatus for a radiation image obtained by a digital radiation imaging unit, comprising: an obtaining unit configured to obtain first dark current data obtained in a state in which the digital radiation imaging unit is not irradiated with radiation before radiation imaging is performed by irradiating the digital radiation imaging unit with radiation, a radiation image obtained by radiation imaging, and second dark current data obtained in a state in which the digital radiation imaging unit is not irradiated with the radiation after the radiation imaging; a generation unit configured to generate correction data in which specified frequency components of at least one of the first and second dark current data are relatively emphasized compared to corresponding frequency components of the other of the first and second dark current data by compositing the first dark current data and the second dark current data; and a correction unit configured to correct the radiation image obtained by the obtaining unit based on the generated correction data.

According to another aspect of the present invention there is provided a radiation system comprising: the above-described image processing apparatus; a radiation detector for detecting radiation in a two-dimensional detection region; and a display unit configured to display radiation image data corrected by the correction unit.

According to a further aspect of the present invention there is provided an image processing method comprising the steps of: obtaining first dark current data obtained in a state in which the digital radiation imaging unit is not irradiated with radiation before radiation imaging performed by irradiating the digital radiation imaging unit with the radiation, a radiation image obtained by the radiation imaging, and second dark current data obtained in a state in which the digital radiation imaging unit is not irradiated with the radiation after the radiation imaging; generating correction data in which specified frequency components of at least one of the first and second dark current data are relatively emphasized compared to the corresponding frequency components of the other of the first and second dark current data by compositing the first dark current data and the second dark current data; and correcting the obtained radiation image based on the generated correction data.

Further features of the present invention will become apparent from the following description of exemplary embodiments with reference to the attached drawings.

BRIEF DESCRIPTION OF THE DRAWINGS

FIG. 1 is a block diagram showing an example of the arrangement of an imaging apparatus according to the first embodiment;

FIG. 2 is a flowchart showing processing of the imaging apparatus according to the first embodiment;

FIG. 3C is a diagram showing the concept of image processing of the image generation unit according to the first embodiment;

FIG. 5C is a diagram showing the concept of image processing of an image generation unit 13 according to the third embodiment; and FIG. 5D is a graph for explaining weighting coefficients.

DESCRIPTION OF THE EMBODIMENTS

Figure 3A:
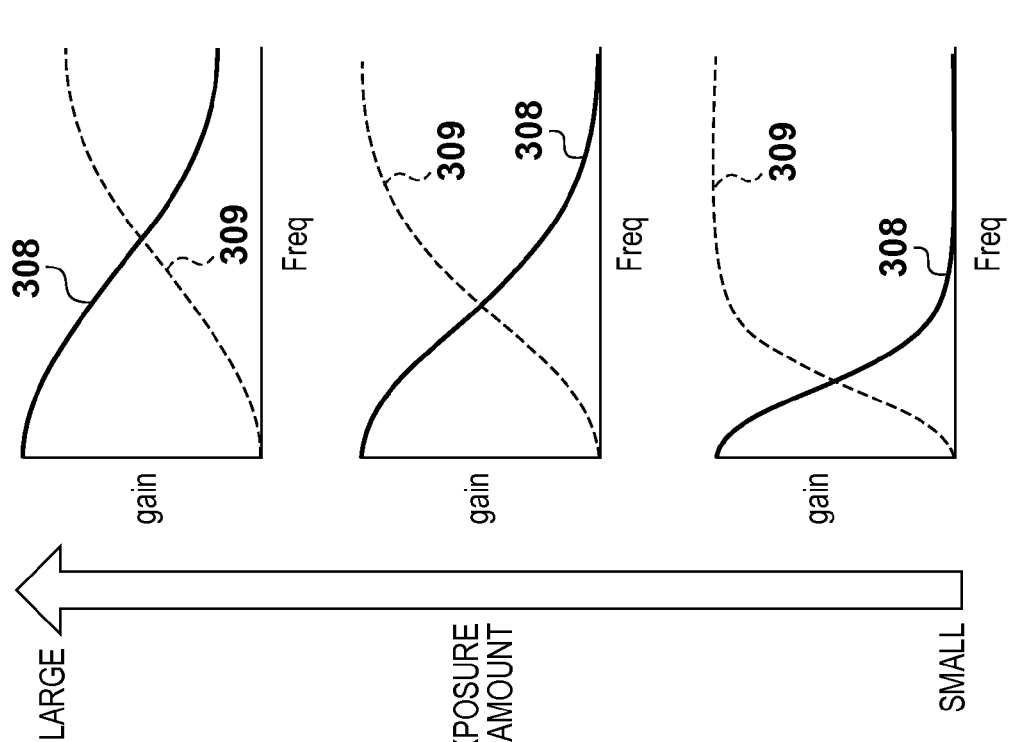
FIG. 3A is a flowchart showing the processing sequence of an image generation unit according to the first embodiment.

Preferred embodiments of the present invention will be described hereinafter with reference to the accompanying drawings. Note that the following embodiments will explain a case in which an example of an image processing apparatus of the present invention is applied to a radiation imaging apparatus.

First Embodiment

The arrangement of an imaging apparatus according to the first embodiment will be described first with reference to FIG. 1. FIG. 1 is a block diagram showing an example of the arrangement of an imaging apparatus which captures a radiation image according to the first embodiment. An imaging apparatus 10 of the first embodiment includes an image obtaining unit 11, memory 12, image generation unit 13, correction processing unit 14, image processing unit 15, display unit 16, image storage unit 17, control unit 18, and operation unit 19.

The image obtaining unit 11 obtains a captured radiation image and dark current data. The dark current data is obtained while no radiation is being emitted and is for the purpose of removing dark current noise or the like, and it will be referred to as "dark current data" or a "dark image" hereinafter. The image generation unit 13 generates correction data by changing a ratio of frequency components of the obtained dark current data. The correction processing unit 14 corrects offset components of the radiation image based on the generated correction data. In generating the correction data, the image generation unit 13 changes the ratio of frequency components based on, for example, coefficients which are set in advance for respective frequency bands.

As another example, the image generation unit 13 decides a degree of change of frequency components based on the radiation image data, dark current data, or the characteristics of an output signal of a radiation detector. Furthermore, the image generation unit 13 changes frequency components using the decided degree of change. In this way, appropriate offset data according to the obtained image can be obtained. The corrected image is displayed on the display unit 16 under the control of the control unit 18.

The image obtaining unit 11 obtains, using a signal detector 111 which functions as a radiation detector that detects radiation by a two-dimensional detection region:

dark current data (first dark current data) obtained by executing imaging in a state in which no radiation is generated from a radiation generator 20. This is performed before a radiation imaging process executed by causing radiation to be emitted from the radiation generator 20 and detecting the radiation using the signal detector 111;

a radiation image obtained by the radiation imaging process; and dark current data (second dark current data) obtained by executing imaging in a state in which no radiation is generated from the radiation generator 20, after the radiation imaging process.

The image generation unit 13 generates correction data by reducing low-frequency components of the first dark current data. The image generation unit 13 further generates correction data by reducing high-frequency components of the second dark current data. In this case, the image generation unit 13 applies image processing for relatively emphasizing a first frequency band in the first dark current data compared to the second dark current data. Also, the image generation unit 13 applies image processing for relatively emphasizing a second frequency band in the second dark current data compared to the first dark current data. An image as an application target is at least either the first dark current data or second dark current data. In another viewpoint, the image generation unit 13 obtains first correction data obtained by lowering a ratio of frequency components on the low-frequency band side of the first dark current data with respect to those on the high-frequency band side. Also, the image generation unit 13 obtains second correction data by lowering a ratio of frequency components on the high-frequency band side of the second dark current data with respect to those on the low-frequency band side. The correction processing unit 14 corrects the radiation image based on the generated first and second correction data.

The image obtaining unit 11 includes the signal detector 111 and an A/D converter 112, and converts object information as information of a target object into digital data. The signal detector 111 includes a sensor unit configured by two-dimensionally arrayed solid-state imaging elements made up of single-crystal silicon or amorphous silicon, and a wavelength conversion member as a material for wavelength-converting radiation from the radiation generator 20 into visible light. As such a wavelength conversion member, for example, CsI:Tl, $Gd_2O_2S$:Tb, and the like are suitably used. The signal detector 111 detects information of radiation transmitted through a target object and converted into visible light by the wavelength conversion member, and converts the visible light into an electrical signal using the solid-state imaging elements. The A/D converter 112 converts the electrical signal output from the signal detector 111 into digital data. Note that in the image obtaining unit 11, the signal detector 111, which functions as the radiation detector, and the A/D converter 112 may be configured as independent units. In this case, the image obtaining unit 11 has a function as an interface for obtaining a radiation image and dark current data obtained from the radiation detector.

The memory 12 is used to store image data obtained by the image obtaining unit 11, and those generated by the image generation unit 13. The memory 12 includes an object image storage area 121, first dark image storage area 122, second dark image storage area 123, and third dark image storage area 124. An object image obtained by the image obtaining unit 11 is stored in the object image storage area 121.

The image generation unit 13 includes a frequency decomposing unit 131, frequency compositing unit 132, and image information discrimination unit 133. The frequency decomposing unit 131 decomposes a first dark image stored in the first dark image storage area 122 and a second dark image stored in the second dark image storage area 123 into a plurality of frequency components. The frequency compositing unit 132 generates a third dark image by compositing images decomposed by the frequency decomposing unit 131, and stores the third dark image in the third dark image storage area 124. The image information discrimination unit 133 extracts specific image information from the object image, first dark image, and second dark image respectively stored in the storage areas 121 to 123, and adjusts the operations of the frequency decomposing unit 131 and frequency compositing unit 132. Details of these operations will be described later.

The correction processing unit 14 includes a correction unit 141, and outputs image data, dark current noise of which is removed, based on the object image and third dark image. The image data after dark current noise removal undergoes image processing such as tone adjustment and dynamic range adjustment processing by the image processing unit 15, and is then displayed by the display unit 16 or is stored in the image storage unit 17. The control unit 18 controls the respective units of the imaging apparatus 10 according to user operations input to the operation unit 19. The radiation generator 20 generates radiation in accordance with an exposure instruction from the control unit 18.

The sequence of processing executed when the imaging apparatus 10 of the first embodiment corrects dark current noise will be described below with reference to FIGS. 1 and 2. FIG. 2 is a flowchart showing the processing sequence executed when the imaging apparatus 10 of the first embodiment corrects dark current noise upon continuously obtaining images. Note that cooperative operations of the respective units according to this processing sequence are managed and controlled by the control unit 18.

Steps S201 to S204 indicate processes to be executed by the image obtaining unit 11 and memory 12. In step S201, the image obtaining unit 11 executes dark imaging. The dark imaging of this step is executed prior to imaging of an object, and a plurality of dark images are obtained. Also, an exposure time of the dark imaging of this step need not be equal to that at the time of object imaging, but they are desirably set to be closer to each other so that, for instance, heat-related frequency artifacts are similar in the dark images and the object image. The dark imaging may be executed using a plurality of exposure times, and an exposure time closest to that used for object imaging may be selected for use in correction.

In step S202, a processing unit (not shown with that name) applies processing for reducing random noise to dark current data obtained from the radiation detector before an image of an object is captured. Such processing unit is implemented by the control unit 18 in this embodiment. That is, in step S202, the control unit 18 executes average processing of dark images obtained in step S201 to composite them into a first dark image. The composited first dark image is stored in the first dark image storage area 122. The average processing of this embodiment is executed to reduce random noise of the first dark image. Since random noise components in an image are reduced to about $1/\sqrt{N}$ by averaging N images, the number (N) of dark images obtained in step S201 is desirably as large as possible. Note that step S202 uses the average processing to remove random noise. However, the present invention is not limited to this, and the first dark image may be generated using known random noise reduction processing. When a first dark image can be generated from one dark image, a plurality of dark images do not need to be acquired in step S201.

Note that the obtaining processes of the first dark image in steps S201 and S202 need not be executed for each imaging of an object. For example, a plurality of dark images may be captured once per day to generate a first dark image, and that first dark image may be commonly used. Alternatively, a first dark image may be generated every time object imaging is done a predetermined number of times, and may be updated. The first dark image is obtained by averaging a plurality of dark images, but a single dark image may be used intact as the first dark image. This is because since the first and second dark images are composited, as described above, a noise reduction effect can be obtained even if the single dark image is used as the first dark image. Also, when a plurality of dark images are obtained for a plurality of different types of exposure times, as described above, a first dark image is obtained for each exposure time, and is stored in the first dark image storage area 122 for each exposure time. Then the first dark image associated with the exposure time closest to that upon obtaining an object image is used.

Next, in step S203, the image obtaining unit 11 captures $n^{th}$ object image. The obtained $n^{th}$ object image is stored in the object image storage area 121. "n" is what is called the "imaging number" herein, and n=1 for the first object imaging. In step S204, the image obtaining unit 11 executes dark imaging to obtain $n^{th}$ second dark images. The dark imaging of this step is executed immediately after the object imaging using an exposure time nearly equal to that of the object imaging. That is, by accumulating an electrical signal on the radiation detector without irradiating radiation using the same accumulation time as that upon the object imaging, a second dark image as second dark current data is obtained. Thus, dark current noise components included in the $n^{th}$ second dark image are approximate to those included in the $n^{th}$ object image. The $n^{th}$ second dark image obtained in this step is stored in the second dark image storage area 123.

Steps S205 to S207 indicate processes to be executed by the image generation unit 13. Random noise components of the first dark image are suppressed by the average processing, as described above, but the obtaining timing of the first dark image is different from that of the object imaging. Hence, changes of dark current noise components due to external factors such as influences of a temperature change during that interval and exposure cannot be reflected. Therefore, as the number n of images to be obtained increases, the difference from dark current noise included in the $n^{th}$ object image tends to increase, too. For this reason, correction using the first dark image alone has the ability to suppress an increase of random noise components as a result of correction but artifacts due to correction errors are readily generated.

By contrast, dark current noise components of each second dark image are close to those included in an object image, but random noise components are not suppressed. Therefore, correction using the $n^{th}$ second dark image alone has little susceptibility to generation of artifacts due to correction errors, but an increase of random noise components due to correction cannot be suppressed.

In this embodiment, by frequency-decomposing and compositing the first and second dark images, there is produced a third dark image which can suppress an increase of random noise components due to correction while reducing artifacts due to correction errors, and an object image is corrected using the third dark image. Note that many dark current noise changes due to external factors caused by influences of a temperature change and exposure are characterized by being included in a low-frequency band. Hence, in this embodiment, frequency compositing processing is executed, so that a ratio of the first dark image is increased in a high-frequency component region (i.e., to give a high high-to-low frequency ratio), and that of the second dark image is increased in a low-frequency component region (i.e. to give a high low-to-high frequency ratio). That is, the third dark image is generated by compositing the first and second dark images, so that the ratio between high and low frequencies after composition of the first dark image becomes larger on the high-frequency component side, and that after composition of the second dark image becomes large on the low-frequency component side. Note that the degree of change in dark current noise varies depending on external factors such as temperature changes and an afterimage generated by imaging. Hence, in this embodiment, ratios at the time of composition are changed based on information relating to captured images.

In step S205, the image information discrimination unit 133 of the image generation unit 13 obtains image information of images obtained by the image obtaining unit 11 based on the $n^{th}$ object image. In step S206, the frequency decomposing unit 131 decomposes the first dark image and the $n^{th}$ second dark image into two or more images respectively including different frequency components. In step S207, the frequency compositing unit 132 composites the images, which are frequency-decomposed in step S206, to obtain an $n^{th}$ third dark image. The composited $n^{th}$ third dark image is stored in the third dark image storage area 124. Note that of the decomposing ratio in step S206 and the compositing ratio in step S207, at least one is controlled based on information (luminance information is used in the first embodiment) of the $n^{th}$ object image obtained in step S205.

Step S208 is a process executed by the correction processing unit 14. In this step, the $n^{th}$ third dark image is subtracted from the $n^{th}$ object image to remove dark current noise, thus outputting images in which dark current noise is corrected. However, the dark current noise correction method used in this step is not limited to the method of subtracting a dark image from an object image, and various other existing methods may be used. Whether or not to end imaging is determined in step S209. If imaging is to be continued, the imaging number n is incremented by 1 in step S210, and the process returns to step S203 to repeat the processes for the $(n+1)^{th}$ imaging.

Details of the processing of the image generation unit 13 will be described below with reference to FIGS. 3A to 3C. In this embodiment, an exposure amount at the time of imaging, which is estimated from luminance information of an object image, is used as image information to be obtained by the image information discrimination unit 133. Also, the frequency decomposing unit 131 decomposes an image into high-frequency components using a low-pass filter (with a normalised Gaussian kernel) given by:

$$LPF(x, y) = \frac{1}{2\pi\sigma^2}\exp\left(-\frac{x^2+y^2}{2\sigma^2}\right) \quad (1)$$

and low-frequency components using a high-pass filter given by:

$$HPF(x,y)=1-LPF(x,y) \quad (2)$$

Figure 3B:
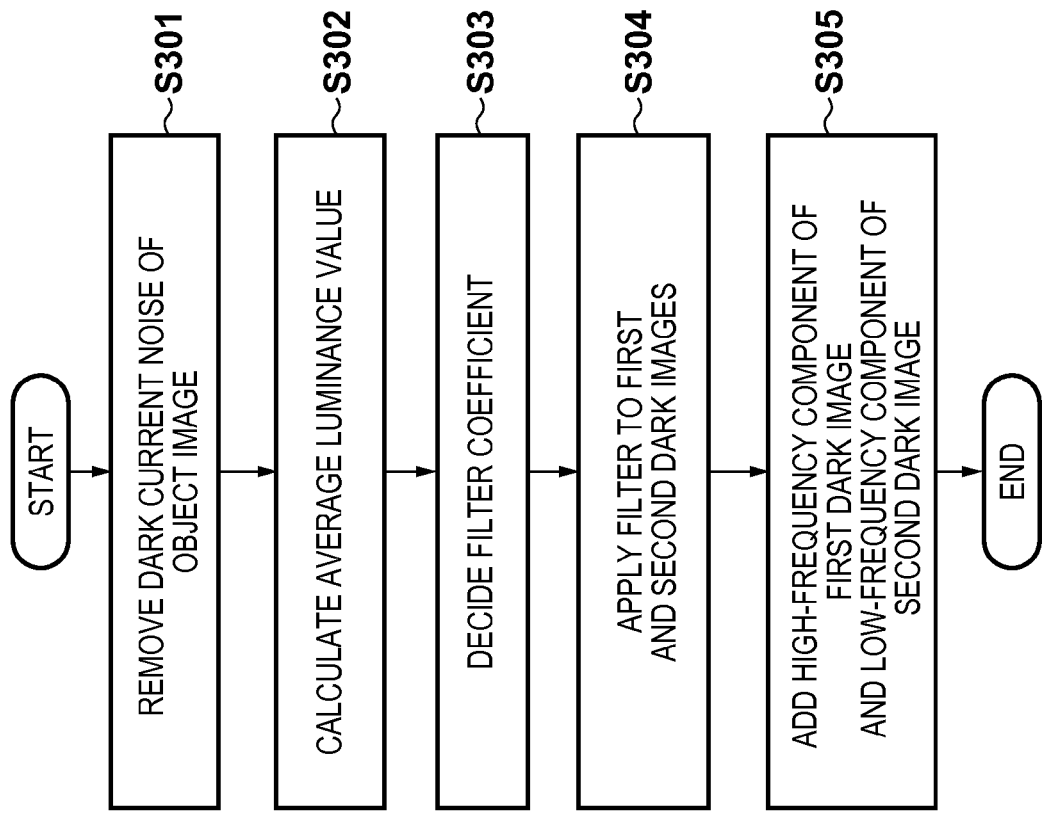
FIG. 3B is a view showing the relationship between magnitudes of exposure amounts and frequency characteristics of filters of the image generation unit.

FIG. 3A is a flowchart showing the processing sequence of the image generation unit 13 according to the first embodiment. FIG. 3B shows the relationships between magnitudes of exposure amount values and the frequency characteristics of the filters. FIG. 3C shows the concept of the image processing of the image generation unit 13 according to the first embodiment.

Steps S301 to S303 indicate processes to be executed by the image information discrimination unit 133. In step S301, the image information discrimination unit 133 removes the influence of dark current noise from an object image. In this step, in order to remove the influence of dark current noise more accurately, the image information discrimination unit 133 subtracts the second dark image from the object image. In step S302, for example, the image information discrimination unit 133 calculates an average luminance value from the object image after correction obtained in step S301, and uses this value as an exposure amount at the time of imaging. The average luminance value may be calculated for the entire image, or a specific region of interest may be generated from an object image, and the average luminance value in that region may be calculated.

In step S303, the image information discrimination unit 133 decides a coefficient of a filter used in frequency decomposing processing based on the exposure amount calculated in step S302. FIG. 3B shows the relationships between the magnitudes of exposure amount values and the frequency characteristics of filters. When the exposure amount assumes a large value, a change of dark current noise becomes large. For this reason, a filter coefficient σ in equation (1) above is set to be small to increase low-frequency components passed through a low-pass filter 308, and to decrease high-frequency components passed through a high-pass filer 309. Conversely, when the exposure amount assumes a small value, the filter coefficient σ in equation (1) above is set to be large. That is, the filter coefficient is set, so that as the object image has a higher luminance value (exposure amount), the passing band of the low-pass filter 308 is broadened, and that of the high-pass filter 309 is narrowed down. Note that the average luminance value is used as the exposure amount in the above description. However, the present invention is not limited to this. For example, a maximum value, minimum value, standard deviation, or the like of the luminance values may be used as the exposure amount.

As shown in FIG. 3C, high-frequency components 303 obtained by applying the high-pass filter 309 to the first dark image and low-frequency components 305 obtained by applying the low-pass filter 308 to the second dark image are used to composite a third dark image 307 (third dark current data). Therefore, when the exposure amount assumes a larger value, more low-frequency components of the second dark image are reflected to the third dark image, thus preferentially taking a measure against a change of dark current noise. On the other hand, when the exposure amount assumes a smaller value (see the bottom of FIG. 3B), more high-frequency components of the first dark image are reflected to the third dark image, thus preferentially assuring a random noise reduction effect. Note that the filter coefficient σ may be decided using a relational expression of an average luminance and the filter coefficient, or the relationships between average luminance values and frequency bands to be used at the time of compositing processing may be calculated in advance, and may be prepared as an LUT (look-up table).

Step S304 is a process to be executed by the frequency decomposing unit 131. The frequency decomposing unit 131 applies the high-pass filter 309 and low-pass filter 308, to which the filter coefficient decided in step S303 is applied, to the first dark image 301 and second dark image 304. Thus, the frequency decomposing unit 131 decomposes the first dark image into low-frequency components 302 and high-frequency components 303, and the second dark image into low-frequency components 305 and high-frequency components 306.

Step S305 is a process to be executed by the frequency compositing unit 132. In this step, the frequency compositing unit 132 adds the high-frequency components 303 of the first dark image and the low-frequency components 305 of the second dark image, thus compositing a third dark image 307.

Note that FIG. 3C shows a state in which the low-frequency components 302 are generated from the first dark image 301, and the high-frequency components 306 are generated from the second dark image 304. However, these processes are not required in practice, and may be omitted.

As described above, according to this embodiment, since a dark image to which a change of dark current noise is reflected while reducing an increase in random noise caused by dark current noise correction can be generated, a decrease in signal-to-noise ratio can be suppressed while reducing artifacts generated due to correction errors. Note that in the example of the above description, a two-dimensional Gaussian filter, which is given by equation (1), is used as the filter. However, the scope of the present invention is not limited to this, and any other existing filters may be used. In the first embodiment, the image information discrimination unit 133 obtains exposure information of an object, and a third dark image is composited using this information. However, the present invention is not particularly limited to this, and frequency decomposing/compositing parameters may be fixed without providing the image information discrimination unit 133.

Second Embodiment

A radiation imaging apparatus according to the second embodiment of the present invention will be described below. In the first embodiment, the image information discrimination unit 133 estimates an exposure amount of an object image, and sets a filter coefficient used by the frequency decomposing unit 131 accordingly. However, in the second embodiment, a filter coefficient is set based on the amount of change ("change amount") of dark current noise. Note that in the second embodiment, since components other than the image information discrimination unit 133 are the same as those in the first embodiment, the same reference numerals denote the same components as in the first embodiment, and a detailed description thereof will not be repeated. In the second embodiment, as information to be obtained by the image information discrimination unit 133, a dark current noise change amount between first and second dark images is used.

Figure 4A:
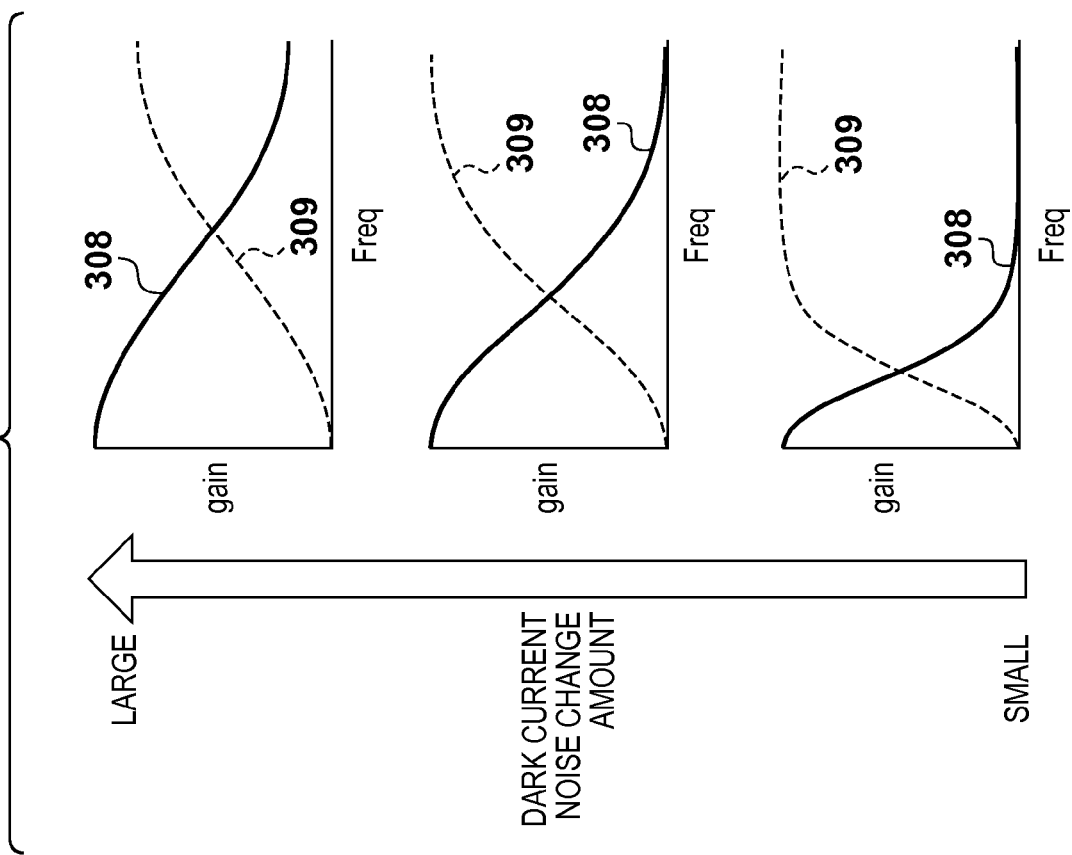
FIG. 4A is a flowchart showing the processing sequence of an image information discrimination unit according to the second embodiment.

Processing of the image information discrimination unit 133 in the second embodiment will be described below with reference to FIGS. 4A and 4B. In this embodiment, the image information discrimination unit 133 functions as a change amount obtaining unit which obtains a change amount of dark current data from first and second dark images. FIG. 4A is a flowchart showing the processing sequence of the image information discrimination unit 133 according to the second embodiment. In step S401, the image information discrimination unit 133 subtracts a first dark image from a second dark image to generate an image which represents a luminance change between the these images. Thus, change information of dark current noise, which has changed between an imaging timing of the first dark image and that of an object image, can be obtained.

In step S402, the image information discrimination unit 133 calculates a dark current noise change amount from the difference image obtained in step S401. As the dark current noise change amount to be calculated from the difference image, arbitrary feature amounts such as an average value, maximum value, minimum value, and standard deviation of pixel values of the difference image may be used. These values may be calculated from the entire difference image or from a specific region of interest, which is set in advance.

In step S403, the image information discrimination unit 133 decides a filter coefficient used in frequency decomposing processing of images based on the dark current noise change amount. FIG. 4B shows the relationships between dark current noise change amount values and frequency characteristics of a low-pass filter 308 and high-pass filter 309. Note that image compositing processing can be implemented by the same arrangement shown in the first embodiment (FIG. 3C). That is, high-frequency components 303 obtained by applying the high-pass filter 309 to the first dark image and low-frequency components 305 obtained by applying the low-pass filter 308 to the second dark image are composited to obtain a third dark image 307.

Figure 4B:
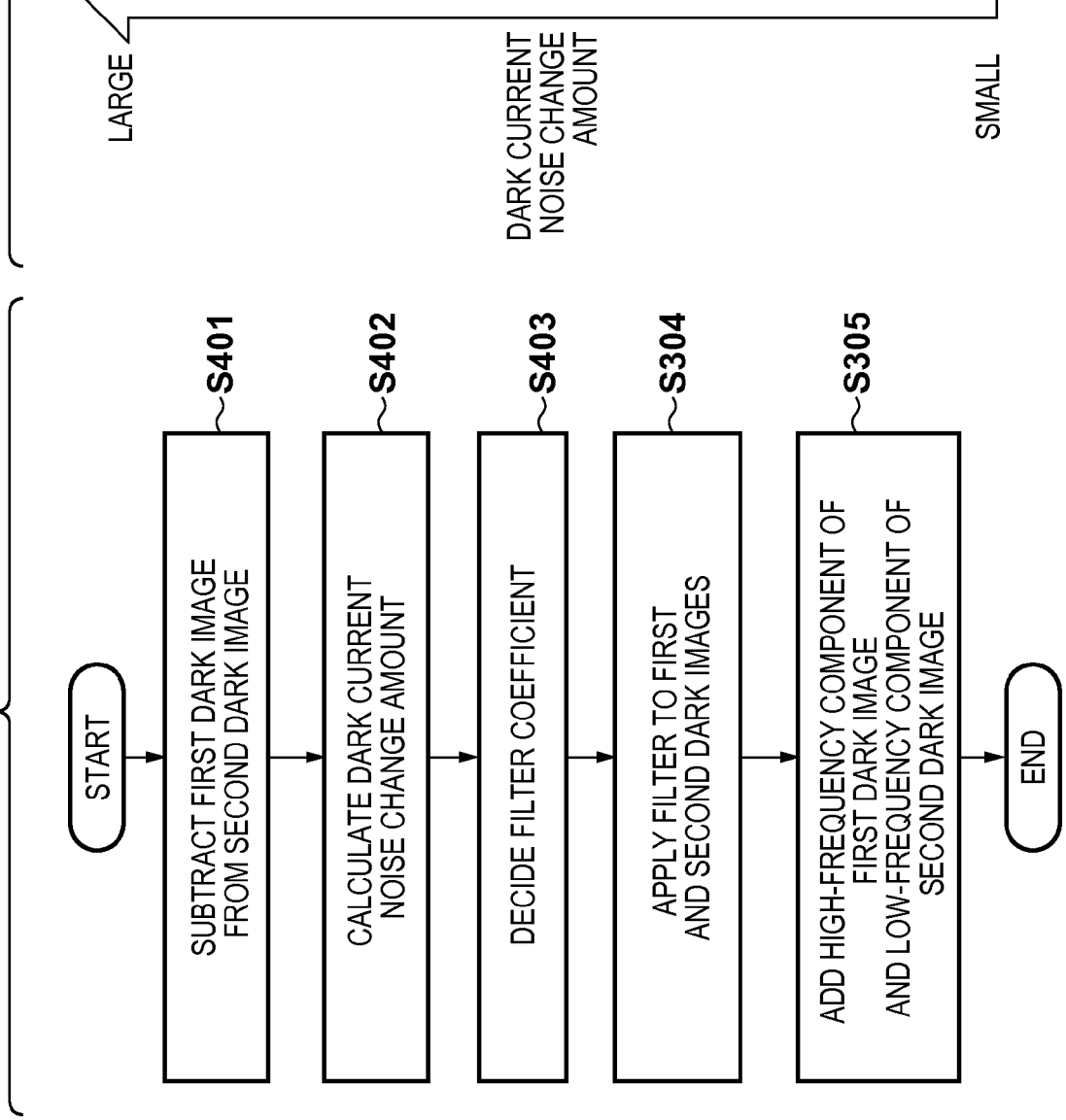
FIG. 4B is a view showing the relationship between magnitudes of dark current noise change amounts and filter frequency characteristics of an image generation unit.

In this embodiment, as shown in FIG. 4B, as the dark current noise change amount assumes a larger value, filter coefficients are set so that a passing band of the low-pass filter 308 is broadened, and that of the high-pass filter 309 is narrowed down. That is, when the dark current noise change amount assumes a larger value, low-frequency components passed through the low-pass filter 308 are increased, and high-frequency components passed through the high-pass filter 309 are decreased. Then, a low-frequency band of the second dark image is reflected more in the third dark image. Conversely, when the dark current noise change amount assumes a smaller value, high-frequency components passed through the high-pass filter 309 are increased, and low-frequency components passed through the low-pass filter 308 are decreased. Then, a high-frequency band of the first dark image is reflected more in the third dark image.

As described above, according to the second embodiment, a random noise reduction effect can be adjusted according to the dark current noise change (or difference) amount. For this reason, even when the dark current noise has changed largely, random noise can be reduced without generating any artifacts due to correction errors on an image. Note that the filter coefficients may be set using both the exposure amount used in the first embodiment and the dark current noise change amount of this embodiment.

Third Embodiment

A radiation imaging apparatus according to the third embodiment of the present invention will be described below. In the first and second embodiments, a decomposing ratio is changed according to an exposure amount (luminance) of an object image or dark current noise change amount during the imaging of an object. The third embodiment will explain processing for changing a compositing ratio. In the first and second embodiments, first and second dark images are decomposed into one each of low- and high-frequency component images to be composited. However, in the third embodiment, first and second dark images are respectively decomposed into a plurality of frequency component images to be composited. Note that in the third embodiment, since components other than an image generation unit 13 are the same as those in the first and second embodiments, the same reference numerals denote the same components as those in the first and second embodiments, and a detailed description thereof will not be repeated. In the third embodiment, in the image generation unit 13, a frequency decomposing unit 131 decomposes each of first and second dark images into a plurality of frequency bands.

Figure 5A:
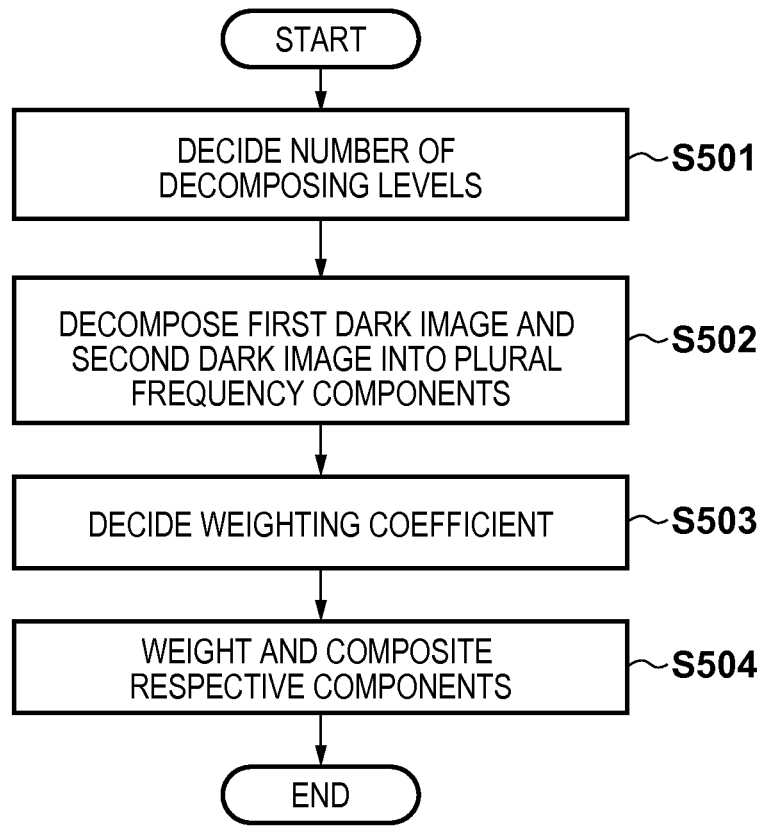
FIG. 5A is a flowchart showing the processing sequence of an image generation unit according to the third embodiment.
Figure 5B:
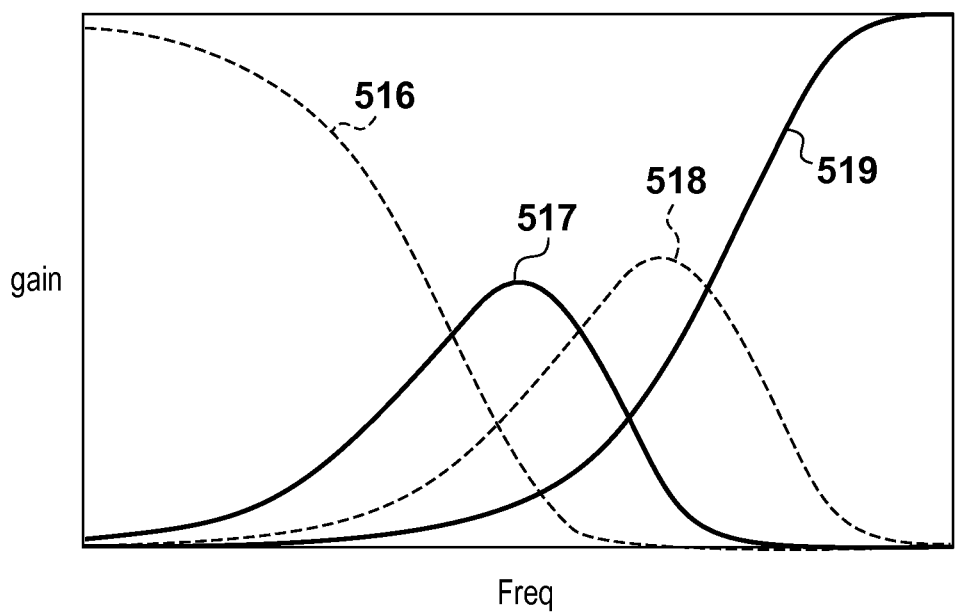
FIG. 5B is a graph showing frequency characteristics of respective decomposing levels of a frequency decomposing unit 131.

Processing of the image generation unit 13 according to the third embodiment will be described below with reference to FIGS. 5A to 5D. FIG. 5A is a flowchart showing the processing sequence of the image generation unit 13 according to the third embodiment.

In step S501, the frequency decomposing unit 131 decides the number m of decomposing levels at the time of the frequency decomposition process. The number m of decomposing levels is decided based on, for example, image size and other image information. An example of the decomposition process using a dark current noise change amount described in the second embodiment as image information will be explained. Alternatively, the number of decomposing levels may be decided using an exposure amount described in the first embodiment. The image information and image size are provided from an image information discrimination unit 133. Note that the number m of decomposing levels may assume a fixed value independently of image size and image information, or may be arbitrarily set by the user.

In step S502, the frequency decomposing unit 131 decomposes a first dark image (I) 501 and second dark image (J) 506 into m frequency components. In this step, a case will be exemplified below wherein Laplacian pyramid decomposing processing is used as the frequency decomposing method, and the number m of decomposing levels=4. In this case, each decomposing level is decomposed according to frequency characteristics shown in FIG. 5B. The first dark image (I) 501 is decomposed into a first decomposed component ($I_1$) 502 having frequency characteristics 516 including many low-frequency components, second decomposed component ($I_2$) 503 having frequency characteristics 517, third decomposed component ($I_3$) 504 having frequency characteristics 518, and fourth decomposed component ($I_4$) 505 having frequency characteristics 519 including many high-frequency components. The second dark image (J) 506 is also decomposed into first to fourth decomposed components ($J_1$) 507 to ($J_4$) 510 having frequency characteristics 516 to 519.

In step S503, a frequency compositing unit 132 decides weighting coefficients $a_i$ used upon adding the respective frequency components of the images obtained in step S502. The weighting coefficients $a_i$ are decided to reflect a low-frequency band of the second dark image more to a third dark image when a dark current noise change amount assumes a larger value, and to reflect a high-frequency band of the second dark image more to the third dark image when the dark current noise change amount assumes a smaller value. For example, relationships between dark current noise change amount values and weighting coefficients shown in FIG. 5D are held in a memory as a table. Weighting coefficients $a_1$ to $a_4$ of this table are decreased as the dark current noise change amount assumes a larger value. That is, the weighting coefficients are set so that as the dark current noise change amount assumes a larger value, an occupation ratio of components of the second dark image in a composite image (third dark image) becomes larger. The frequency compositing unit 132 decides the respective weighting coefficients according to the dark current noise change amount obtained from the difference image between the first and second dark images. Note that the dark current noise change amount used in this case may be calculated using the first dark image (I) 501 and second dark image (J) 506, as described in the second embodiment, or may be calculated for respective frequency decomposed components. In this case, the frequency decomposed components are images of respective frequency decomposed components obtained using the frequency characteristics 516 to 519. A dark current noise change amount calculated for frequency decomposed components is used to set the corresponding weighting coefficient $a_i$. The weighting coefficient $a_i$ may also be calculated dependent on the number of frequency decomposed components; and these two values may be mutually selected to obtain the dark current noise change amount desired.

In step S504, the frequency compositing unit 132 adds the frequency decomposed components $I_i$ and $J_i$ of the respective images obtained in step S502 using the weighting coefficients $a_i$ decided in step S503 based on:

$$K_i = a_i I_i + (1-a_i) J_i \ (i=1,2,\ldots,n) \qquad (3)$$

Thus, the frequency compositing unit 132 generates four frequency components ($K_1$) 511 to ($K_4$) 514 which form the third dark image. After that, the frequency compositing unit 132 composites these frequency components ($K_1$) 511 to ($K_4$) 514 to generate a third dark image (K) 515.

As described above, according to this embodiment, since the compositing ratio between the first and second dark images can be changed more finely compared to the arrangements of the first and second embodiments, dark current noise can be corrected more accurately while suppressing a decrease in signal-to-noise ratio. Note that Laplacian pyramid decomposing processing has been exemplified as the method of decomposing an image into a plurality of frequency components and compositing them. However, the present invention is not limited to this choice of processing. For example, any other decomposing methods of the first and second dark images such as wavelet decomposing processing may be used. Also, this embodiment has exemplified the case in which the dark current noise change amount described in the second embodiment is used as image information. However, the scope of the present invention includes use of an exposure amount described in the first embodiment.

In the aforementioned embodiments, dark current data obtained before imaging and those obtained after imaging are used in correction. However, the present invention is not limited to this, and dark current data immediately after imaging and those after an elapse of a predetermined period of time may be used.

In the aforementioned embodiments, dark current data obtained before imaging and those obtained after imaging are composited. However, these data need not always be composited, and the same effects can be obtained by subtracting processed dark current data from a radiation image as correction data.

As another example, radiation image data obtained by subtracting correction data using dark current data obtained before imaging is displayed initially, and radiation image data obtained by further subtracting correction data using dark current data obtained after imaging is then displayed, thus obtaining an appropriate image while reducing a display delay.

As still another example, after correction data is subtracted in advance in the radiation detector, radiation image data is transferred to a control apparatus, and is displayed as a first display image on the display unit. After the radiation image is transferred, dark current data after imaging are transferred to the control apparatus, and correction data is generated by the processing of the aforementioned embodiments. A difference between the generated correction data and dark current data before imaging is subtracted from the radiation image data displayed on the display unit. Radiation image data after subtraction is displayed on the display unit as a second display image. The initially displayed first display image has undergone offset correction using the dark current data after imaging, and the next displayed second display image is obtained as an image which is accurately corrected using the correction data obtained by the aforementioned processing.

The present invention is not limited to embodiments as the imaging apparatus, and a radiation imaging system configured by a plurality of apparatuses are included in embodiments.

Aspects of the present invention can also be realized by a computer of a system or apparatus (or devices such as a CPU (central processing unit) or MPU (microprocessing unit)) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-055093, filed Mar. 12, 2012 which is hereby incorporated by reference herein in its entirety.

What is claimed is:

1. An image processing apparatus for a radiation image obtained by a digital radiation imaging unit, comprising:
a receiver configured to receive first dark current data, a radiation image obtained by the radiation imaging, and second dark current data, the first dark current data being generated in a state in which the digital radiation imaging unit is not irradiated with radiation before radiation imaging is performed by irradiating the digital radiation imaging unit with the radiation, and the second dark current data being generated in a state in which the digital radiation imaging unit is not irradiated with the radiation after the radiation imaging;
a generation unit, including a processor, configured to generate correction data, by compositing the first dark current data and the second dark current data in which specified frequency components of one of the first and second dark current data are relatively emphasized compared to corresponding frequency components of the other of the first and second dark current data; and
a correction unit, including a processor, configured to correct the radiation image obtained by said receiver based on the generated correction data,
wherein at least one of said processors comprises one of a CPU and an MPU.

2. The apparatus according to claim 1, wherein said generation unit is configured to generate, based on the first dark current data and the second dark current data, correction data in which first frequency components of the first dark current data are relatively emphasized compared to the corresponding first frequency components of the second dark current data, and second frequency components of the second dark current data are relatively emphasized compared to the corresponding second frequency components of the first dark current data.

3. The apparatus according to claim 2, wherein said generation unit is configured to extract the first frequency components from the first dark current data, extract the second frequency components from the second dark current data, and generate the correction data by compositing the extracted first frequency components and the extracted second frequency components.

4. The apparatus according to claim 2, wherein said generation unit is configured to change a ratio of first frequency components to second frequency components based on weighting coefficients set for respective associated frequency bands.

5. The apparatus according to claim 4, further comprising a setting unit, including a processor, configured to set the changed ratio of the frequency components based on the radiation image obtained by said obtaining unit, wherein said processor of said setting unit comprises one of a CPU and an MPU.

6. The apparatus according to claim 5, wherein said setting unit is configured to set the ratio so that the ratio of the second frequency components of the second dark current data to the second frequency components of the first dark current data is increased with increasing luminance of the object.

7. The apparatus according to claim 6, further comprising a change amount obtaining unit, including a processor, configured to obtain a change amount of dark current data from the first dark current data and the second dark current data, and wherein said setting unit is configured to set the ratio so that the ratio of the second frequency components of the second dark current data to the second frequency components of the first dark current data is increased with increasing change amount, wherein said processor of said change amount obtaining unit comprises one of a CPU and an MPU.

8. The apparatus according to claim 1, wherein the specified frequency components are high-frequency components, and said generation unit is configured to generate correction data by reducing low-frequency components of the first dark current data.

9. The apparatus according to claim 1, wherein said generation unit is configured to generate correction data by applying, to at least one of the first dark current data and the second dark current data, image processing for relatively emphasizing a first frequency band in the first dark current data compared to the second dark current data, and relatively emphasizing a second frequency band in the second dark current data compared to the first dark current data.

10. The apparatus according to claim 1, wherein said generation unit is configured to generate first correction data in which a ratio of frequency components on a low-frequency band side with respect to frequency components on a high-frequency band side is decreased in association with the first dark current data, and second correction data in which a ratio of frequency components on a high-frequency band side with respect to frequency components on a low-frequency band side is decreased in association with the second dark current data, and said correction unit is configured to correct the radiation image obtained by the receiver using the first correction data and the second correction data.

11. The apparatus according to claim 10, wherein said generation unit is configured to generate first correction data by applying a high-pass filter to the first dark current data, and second correction data by applying a low-pass filter to the second dark current data.

12. The apparatus according to claim 11, wherein said generation unit is configured to set respective filter coefficients so that a passing band of the low-pass filter is broadened and a passing band of the high-pass filter is narrowed down with increasing luminance of the radiation image data.

13. The apparatus according to claim 11, further comprising a change amount obtaining unit, including a processor, configured to obtain a change amount of dark current from the first dark current data and the second dark current data, wherein said generation unit is configured to set respective filter coefficients so that a passing band of the low-pass filter is broadened and a passing band of the high-pass filter is narrowed down with increasing change amount, wherein said processor of said change amount obtaining unit comprises one of a CPU and an MPU.

14. The apparatus according to claim 1, further comprising a processing unit, including a processor, configured to obtain the first dark current data by applying processing for reducing random noise to the dark current data obtained from a radiation detector before imaging of an object, wherein said processor of said processing unit comprises one of a CPU and an MPU.

15. The apparatus according to claim 14, wherein said processing unit is configured to obtain the first dark current data by averaging a plurality of instances of dark current data.

16. The apparatus according to claim 1, wherein said receiver is configured to obtain the second dark current data by executing imaging in a state in which the digital radiation imaging unit is not irradiated with the radiation during an accumulation time which is equal to an accumulation time of imaging of the radiation image.

17. The apparatus according to claim 1, wherein said generation unit comprises a decomposing unit, including a processor, configured to decompose each of a first dark image and a second dark image into two or more frequency components, and said generation unit is configured to generate the correction data by weighting and compositing the frequency components of the first and second dark images decomposed by said decomposing unit, wherein said processor of said decomposing unit comprises one of a CPU and an MPU.

18. The apparatus according to claim 1, wherein said correction unit is configured to subtract the correction data from the radiation image data.

19. A radiation system comprising:
an image processing apparatus according to claim 1;
a radiation detector for detecting a radiation in a two-dimensional detection region; and
a display unit configured to display radiation image data corrected by said correction unit.

20. An image processing method comprising the steps of:
receiving first dark current data, a radiation image obtained by the radiation imaging, and second dark current data, the first dark current data being generated in a state in which a digital radiation imaging unit that produces the radiation image is not being irradiated with radiation before radiation imaging is performed by irradiating the digital imaging unit with the radiation, and the second dark current data being generated in a state in which the digital radiation imaging unit is not irradiated with the radiation after the radiation imaging;
generating correction data, by compositing the first dark current data and second dark current data, in which specified frequency components of at least one of the first and second dark current data are relatively emphasized compared to the corresponding frequency components of the other of the first and second dark current data; and
correcting the received radiation image based on the generated correction data,
wherein at least one of said steps is performed by at least one of a CPU and an MPU.

21. An image processing method according to claim 20, further comprising the step of generating first correction data by applying a high-pass filter to the first dark current data, and second correction data by applying a low-pass filter to the second dark current data.

* * * * *